United States Patent [19]
Li

[11] Patent Number: 5,439,474
[45] Date of Patent: Aug. 8, 1995

[54] MORCELLATOR SYSTEM

[75] Inventor: Lehmann K. Li, Milford, Conn.

[73] Assignee: Li Medical Technologies, Inc., Trumbull, Conn.

[21] Appl. No.: 134,142

[22] Filed: Oct. 8, 1993

[51] Int. Cl.⁶ .................. A61B 17/32; A61B 19/00
[52] U.S. Cl. ................... 606/184; 606/167; 128/754
[58] Field of Search ............... 128/749-754; 604/19, 22; 606/1, 110, 167, 168, 170, 171, 177, 182-185

[56] References Cited

U.S. PATENT DOCUMENTS

| | | | |
|---|---|---|---|
| 4,282,884 | 8/1981 | Boebel | 128/751 |
| 4,696,298 | 9/1987 | Higgins et al. | 606/171 |
| 5,047,008 | 9/1991 | Juan et al. | 606/171 |
| 5,129,910 | 7/1992 | Phan et al. | 606/127 |
| 5,226,910 | 7/1993 | Kajiyama et al. | 606/171 |

FOREIGN PATENT DOCUMENTS 0537116  4/1993  European Pat. Off. ............ 606/185

Primary Examiner—Stephen C. Pellegrino
Assistant Examiner—Glenn Dawson
Attorney, Agent, or Firm—Pandiscio & Pandiscio

[57]  ABSTRACT

A morcellator device having an inner tube with a cutting edge reciprocatingly mounted within an outer tube. The outer tube has a distal opening with a sharpened surface for receiving tissue therein so that the inner tube may slide distally severing the tissue caught inside the outer tube. Both tubes have barbs mounted so as to project into the lumen of the inner tube which allow the cut tissue to move proximally, but inhibits it's movement distally.

20 Claims, 19 Drawing Sheets

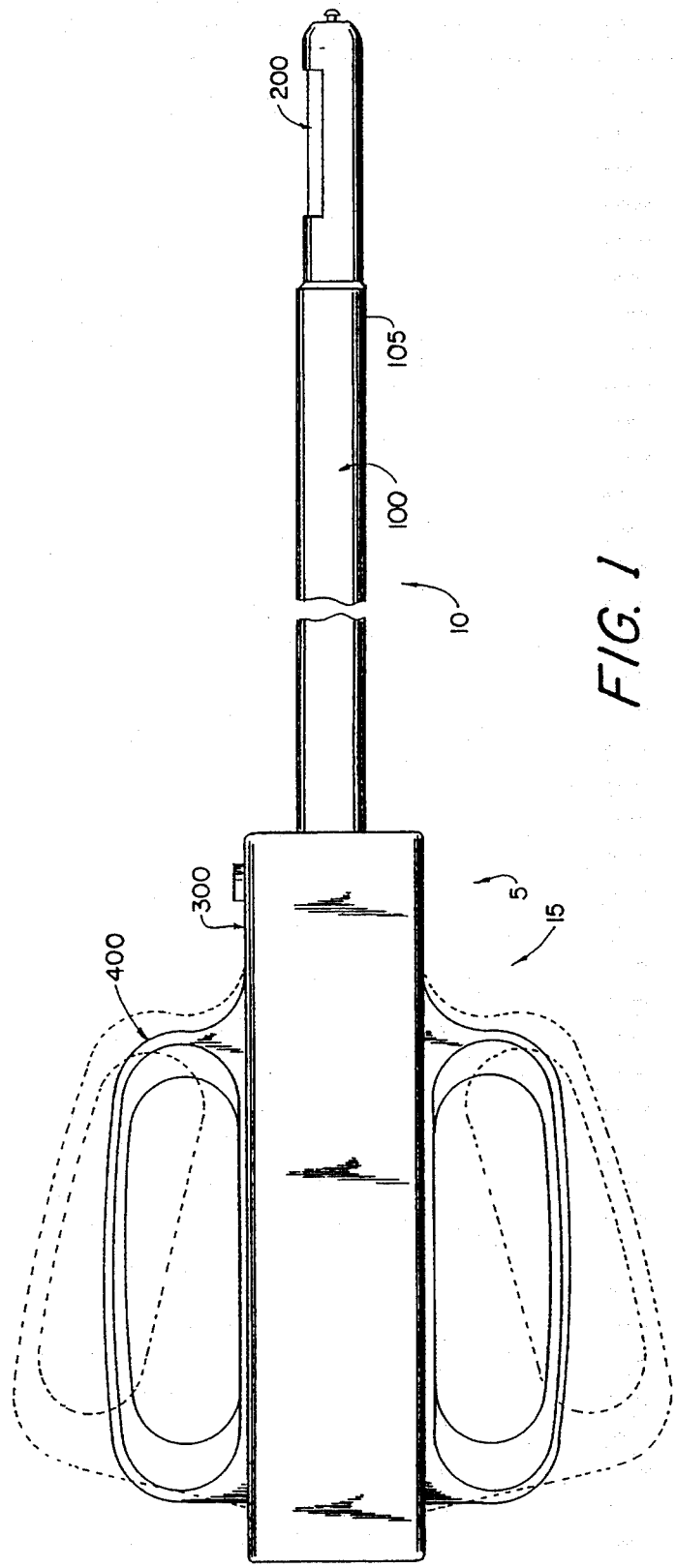
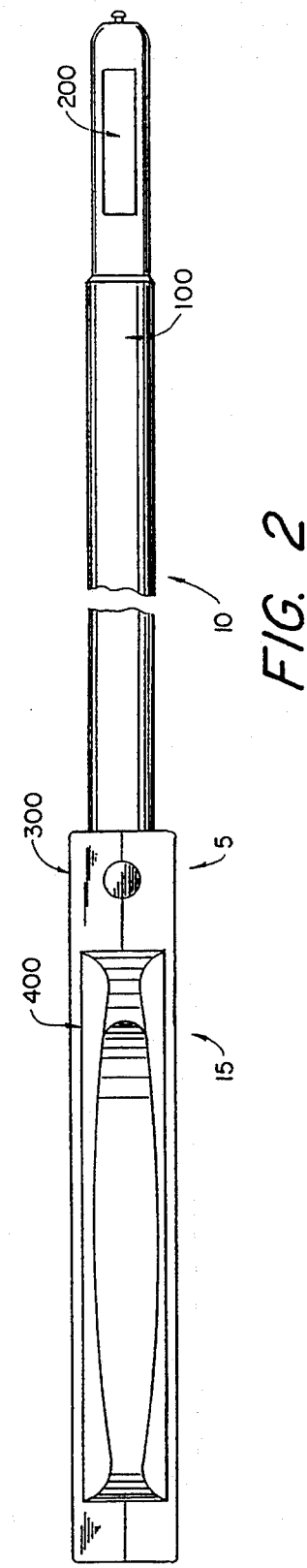
FIG. 1
FIG. 2

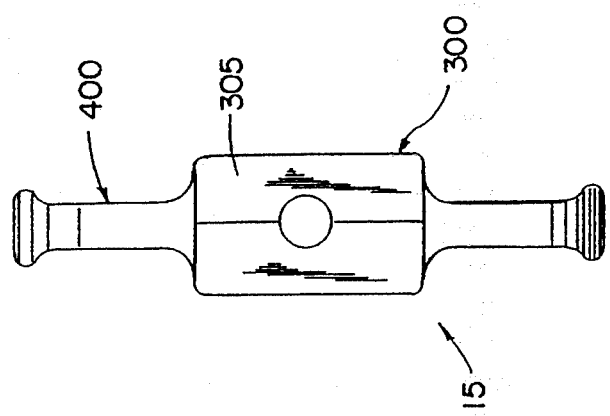
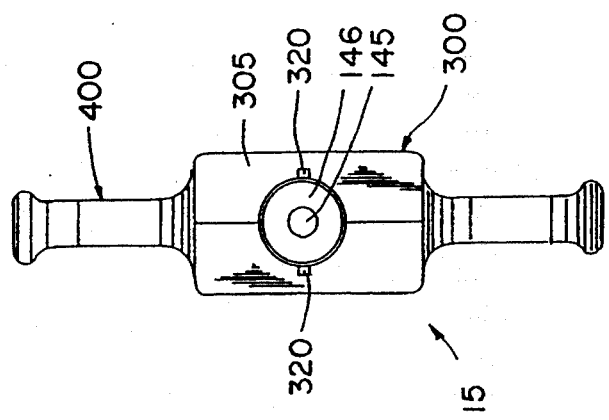

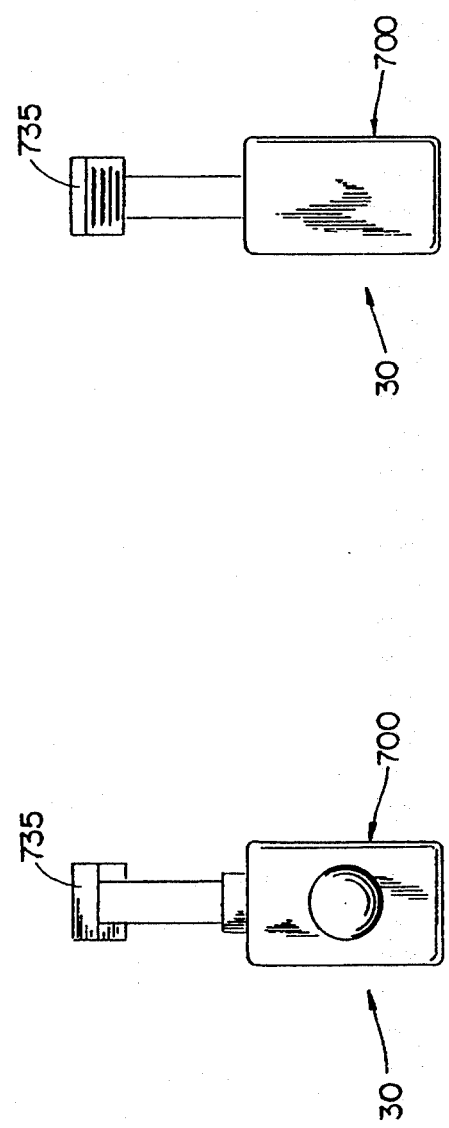

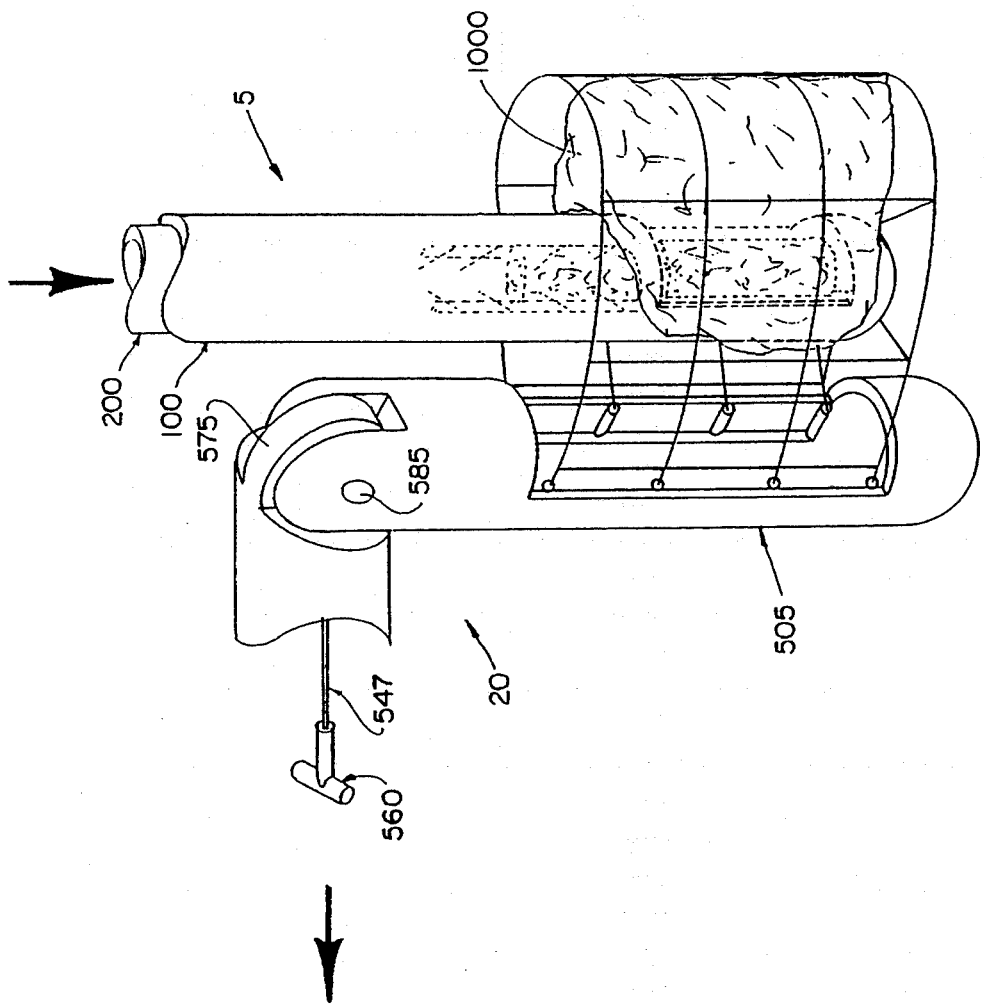

MORCELLATOR SYSTEM

FIELD OF THE INVENTION

This invention relates to laparoscopic surgery in general, and more particularly to apparatus and methods for removing severed tissue from the body during such surgery.

BACKGROUND OF THE INVENTION

In laparoscopic surgery, access is gained to an interior surgical site by making one or more short incisions in the body which extend down to the interior surgical site, and then inserting a hollow tube or cannula into each incision so that the cannulas can act as liners to hold the incisions open and thereby provide portals leading down to the interior surgical site. A laparoscopic procedure can then be performed by passing surgical instruments (e.g. cutting devices, clamps, viewing apparatus, etc.) down the cannulas so that the distal working ends of the instruments can be positioned and used about the surgical site, while the proximal handle ends of the instruments remain outside the body where they can be grasped by the surgeon.

Laparoscopic procedures frequently involve the removal of tissue from the interior surgical site. For example, one of the most common laparoscopic procedures practiced today is the laparoscopic cholecystectomy, in which the patient's gallbladder is removed from the body. In other laparoscopic procedures, other tissue (e.g. an appendix, portions of the intestine, etc.) may be removed from the body. In some situations, the excised tissue is relatively small and can be passed through the narrow cannula opening intact. In other situations, however, the excised tissue is too large to fit through a cannula intact. When this occurs the excised tissue must generally be cut down into a number of smaller pieces before it can be passed through a cannula. For example, in many laparoscopic cholecystectomies, the patient's gallbladder must be dissected into several smaller pieces before it can be removed through a cannula.

Such dissection of the excised tissue can present problems for the surgeon. For one thing, the excised tissue must generally be held in place by one instrument (e.g. a forceps) while it is dissected into several smaller pieces by another instrument (e.g. a cutting tool). These smaller pieces of tissue must themselves be captured by apparatus so that they can be removed from the body. It can be difficult to coordinate the holding, dissecting and capturing of the various pieces of tissue, particularly during laparoscopic surgical procedures where visibility is generally limited and tissue access restricted.

OBJECTS OF THE INVENTION

Accordingly, the principal object of the present invention is to provide apparatus and methods for use in removing tissue from the body during laparoscopic procedures.

Another object of the present invention is to provide a morcellator system for use in laparoscopically dissecting a relatively large piece of tissue while it is located at an interior surgical site, and then removing the resulting smaller pieces of tissue from the body.

Still another object of the present invention is to provide a morcellator device for use in dissecting a relatively large piece of tissue into a number of smaller pieces during a laparoscopic surgical procedure.

Yet another object of the present invention is to provide a morcellator device for use in dissecting a relatively large piece of tissue into a number of smaller pieces during a laparoscopic surgical procedure, wherein the morcellator includes means for capturing those smaller pieces of tissue to the morcellator until the morcellator is removed from the And another object of the present invention is to provide a netting device for use in capturing a relatively large piece of tissue during a laparoscopic surgical procedure.

Still another object of the present invention is to provide a netting device for use in capturing a relatively large piece of tissue during a laparoscopic surgical procedure, wherein the netting device is adapted to be used in conjunction with a morcellator device to laparoscopically capture and dissect a relatively large piece of tissue while it is located at an interior surgical site, and then to remove the resulting smaller pieces of tissue from the body, and further wherein the netting device is capable of progressively closing down in size so as to keep the tissue captured to the netting tool even as it is reduced in size by the morcellator.

Yet another object of the present invention is to provide a morcellator system for use in dissecting a relatively large piece of tissue while it is located at a surgical site and then removing the resulting smaller pieces of tissue from the surgical site, wherein the morcellator system is adapted for use in both laparoscopic and open surgeries.

SUMMARY OF THE INVENTION

These and other objects are addressed by the present invention, which comprises a morcellator system for use in removing relatively large pieces of tissue from the body during laparoscopic surgery. The morcellator system generally comprises a morcellator device and a netting device.

The morcellator device generally comprises an outer tube having a distal end terminating a distal end surface, a proximal end, an internal passageway extending from said distal end to said proximal end, and an opening formed in said distal end and communicating with said interior passageway;

an inner tube having a distal end terminating in a distal end surface, a proximal end, and an interior passageway connecting said distal end with said proximal end, said inner tube being sized to make a close sliding fit within said outer tube;

a handle assembly comprising a body and actuating means, said proximal end of said outer tube being attached to said body, and said proximal end of said inner tube being attached to said actuating means, with said actuating means being adapted to said move said inner tube between (1) a first portion wherein said opening formed in said outer tube is closed off by said inner tube, and (2) a second position wherein said opening formed in said outer tube is at least part way open;

first tissue holding means projecting into the interior of said inner tube for permitting tissue to move proximally through said inner tube, and preventing tissue from moving distally through said inner tube;

second tissue holding means projecting into the interior of said outer tube for permitting tissue to move proximally through said outer tube, and preventing tissue from moving distally through said outer tube.

The netting device generally comprises a shaft having a distal end, a proximal end, and an interior opening extending from said distal end to a proximal opening adjacent said proximal end;

said distal end comprising a hinged upper portion and a fixed lower portion and including at least one counter bore therebetween and a sliding sleeve positioned proximally of said hinged upper portion;

a cylindrical body having an interior passageway, a rounded distal tip and a bifurcated proximal end and further comprising at least one suture manifold located circumferentially within said interior passageway and adapted to guide suture means;

net means deployable from said cylindrical body, said net means comprising a plurality of circumferentially extending segments terminating in a proximal end, a plurality of longitudinally extending segments interconnecting said plurality of circumferentially extending segments, a plurality of radially extending segments defining an end surface, and a net deployment ring positioned on one of said logitudinally extending segments;

a cylinder coupling having an interior passagway, a stepped outer profile adapted to releasably engage said at least one counter bore and further including a distal tongue for mating with said bifurcated proximal end of said cylindrical body; and a handle assembly comprising a body having a central bore, triggering means, and a releasing means positioned on a top surface of said handle asembly, said proximal end of said shaft being attached to said central bore;

retracting means positioned within said interior opening of said shaft comprising advancing means and holding means interconnected to said triggering means and adapted to move said net from: (1) a first, fully deployed position wherein said net is deployed about a relatively large tissue mass, (2) a second partially closed position wherein said tissue mass is held within said net and in close proximity to morcellating means.

BRIEF DESCRIPTION OF THE DRAWINGS

Still other objects and features of the present invention will be more fully disclosed or rendered obvious by the following detailed description of the preferred embodiments of the invention, which are to be considered together with the accompanying drawings wherein like numbers refer to like parts and further wherein:

FIG. 1 is a side view of a morcellator device formed in accordance with the present invention;

FIG. 2 is a top view of the morcellator;

FIG. 4 is a front view of the morcellator's handle assembly;

FIG. 5 is a rear view of the morcellator;

FIG. 12 is a front view of a portion of the netting device's handle assembly;

FIG. 13 is a rear view of the netting device;

FIGS. 23-28 are a series of views showing the morcellator and netting device capturing then dissecting a relatively large piece of tissue within the body.

DETAILED DESCRIPTION OF THE PREFERRED EMBODIMENTS

Figure 3:
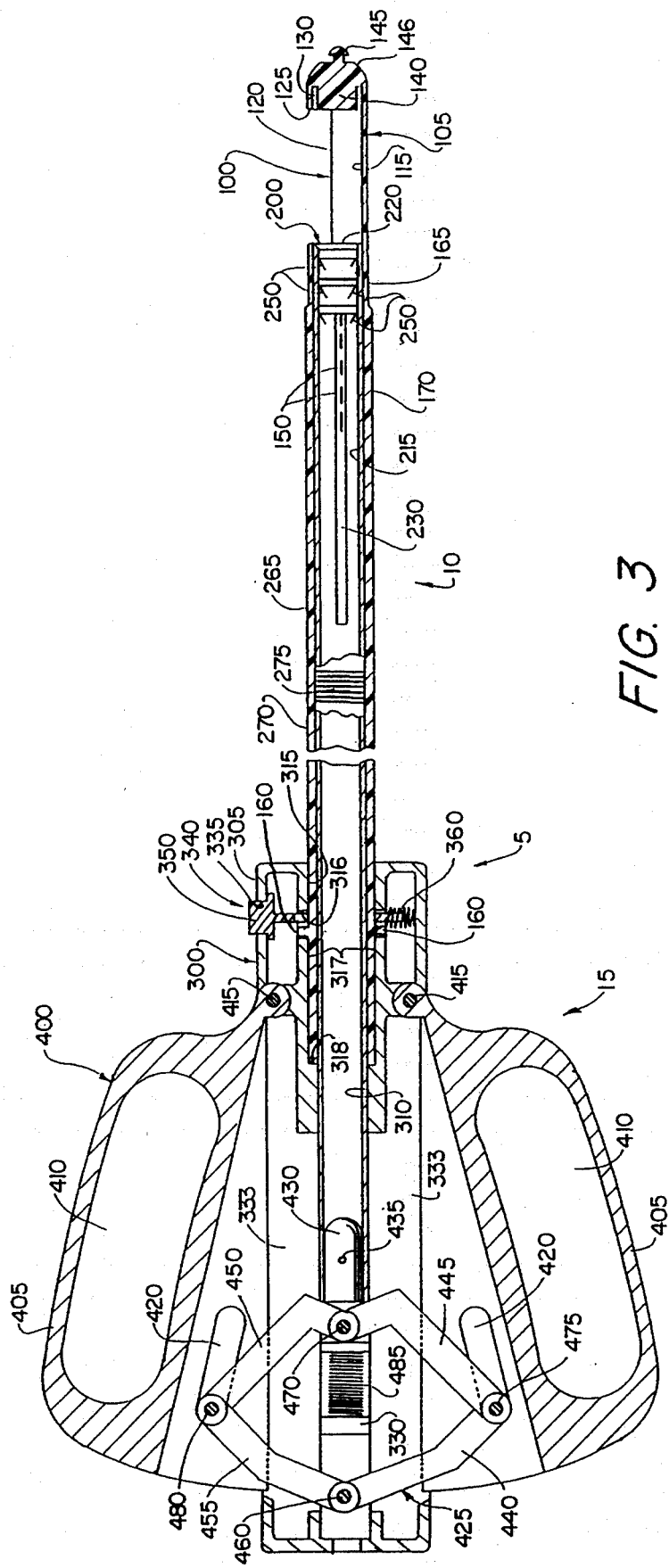
FIG. 3 is a side view in section of the morcellator.
Figure 6:
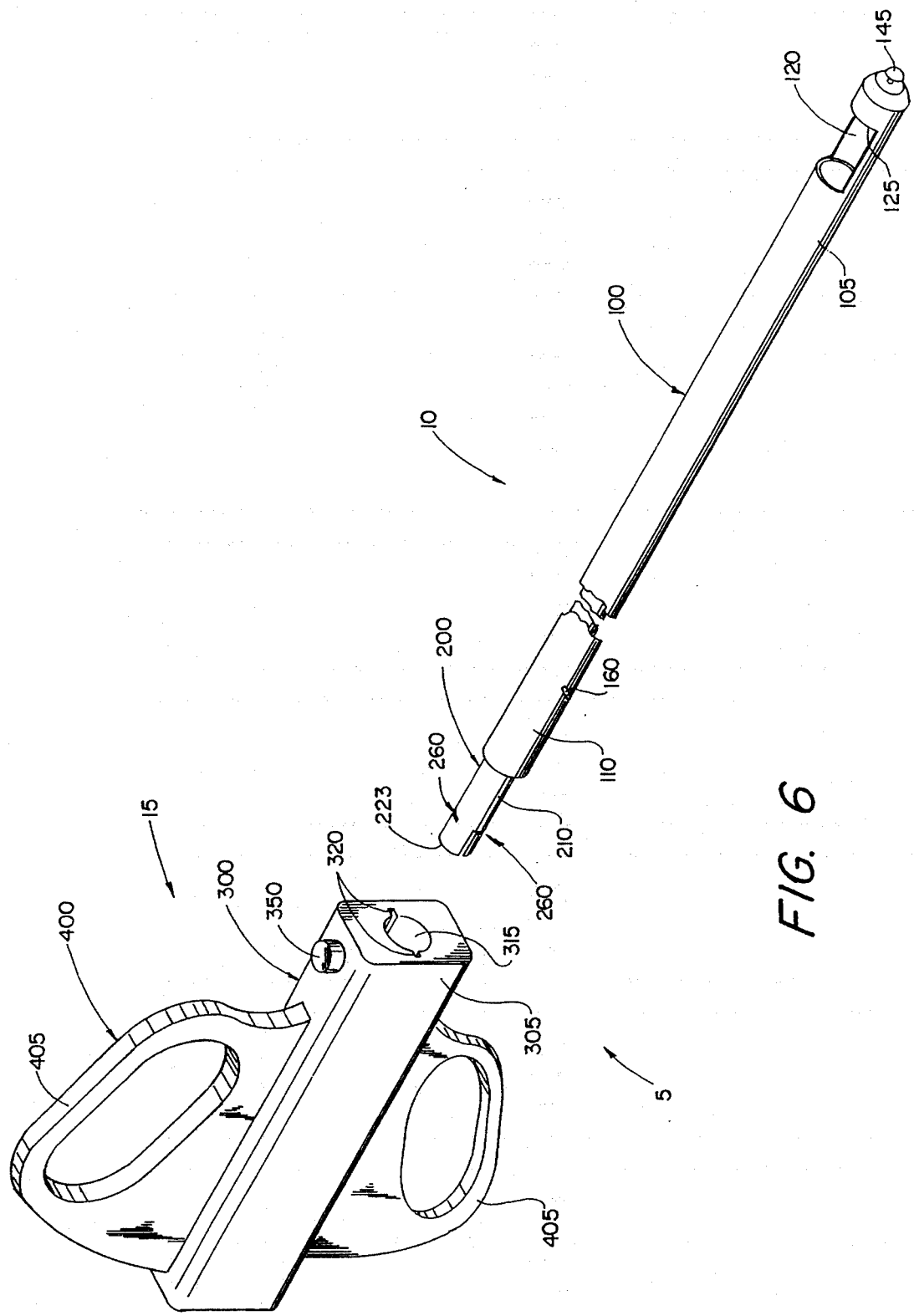
FIG. 6 is a perspective view of the morcellator, wherein the morcellator's cutting assembly is shown in telescoping relation to the morcellator's handle assembly.
Figure 7:
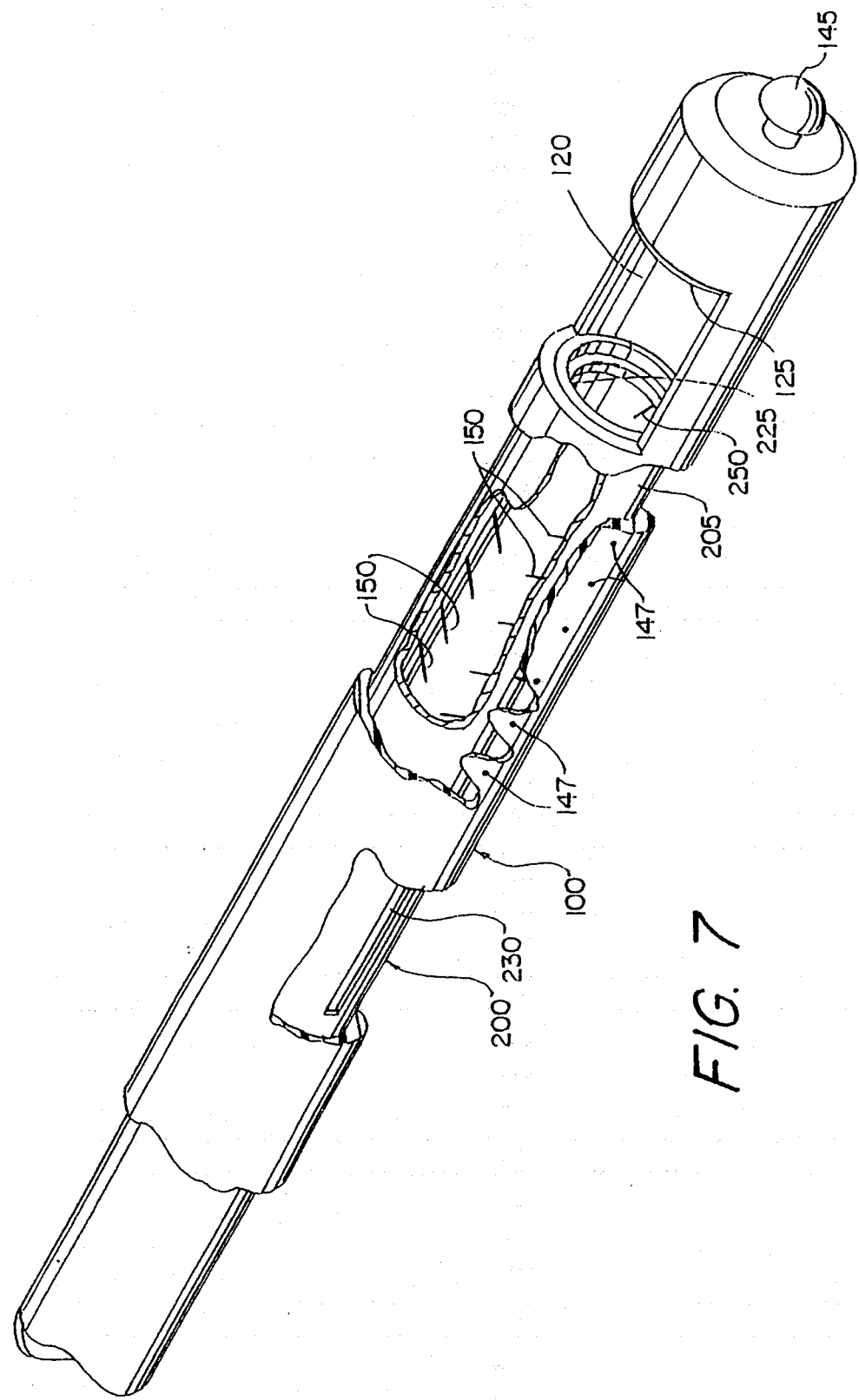
FIG. 7 is a perspective view showing the distal end of the morcellator's cutting assembly, with portions of the assembly's tube members being broken away.
Figure 8:
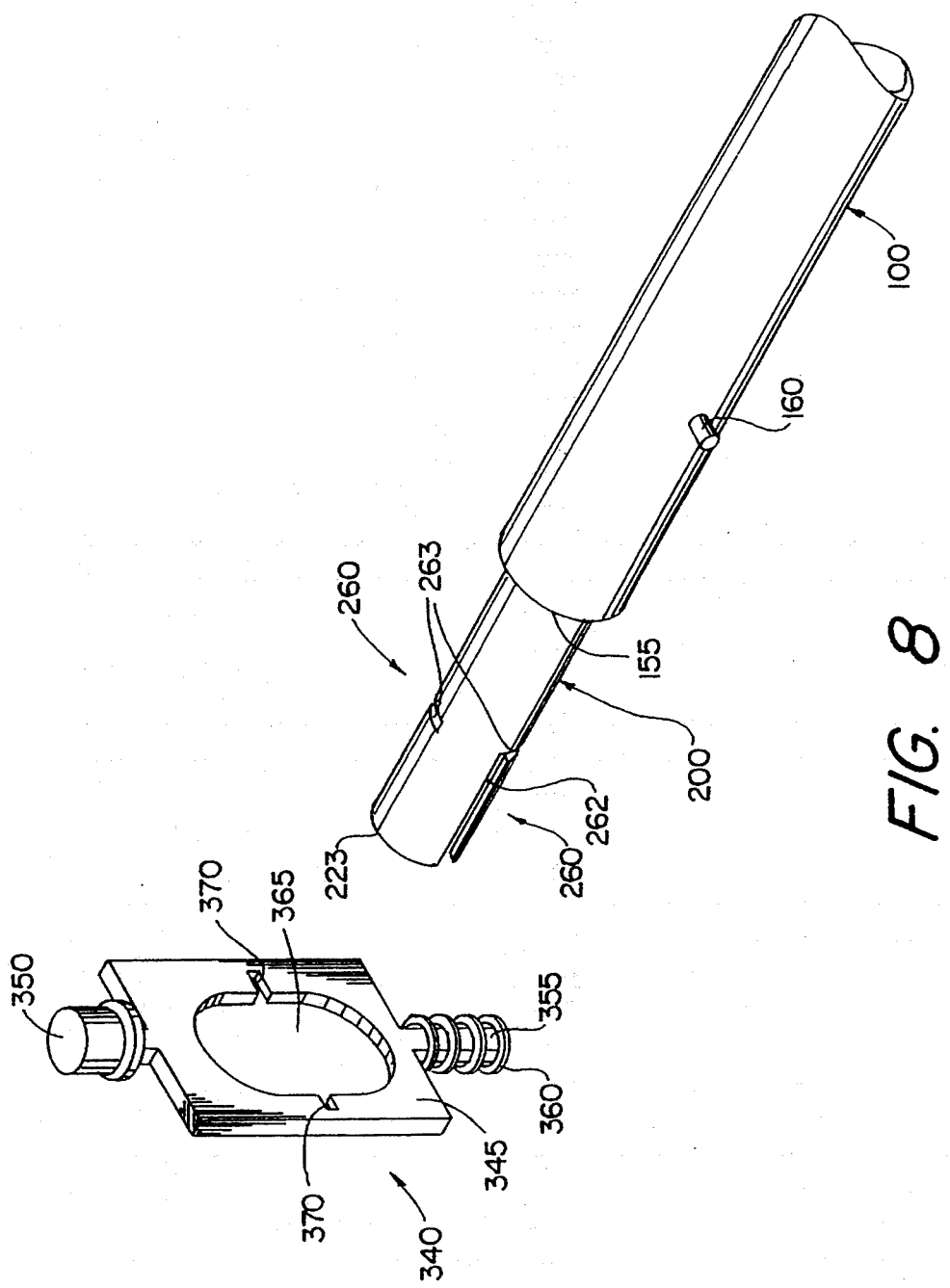
FIG. 8 is a perspective view showing the handle assembly's gate subassembly and the proximal end of the cutting assembly in telescoping relation to one another.
Figure 9:
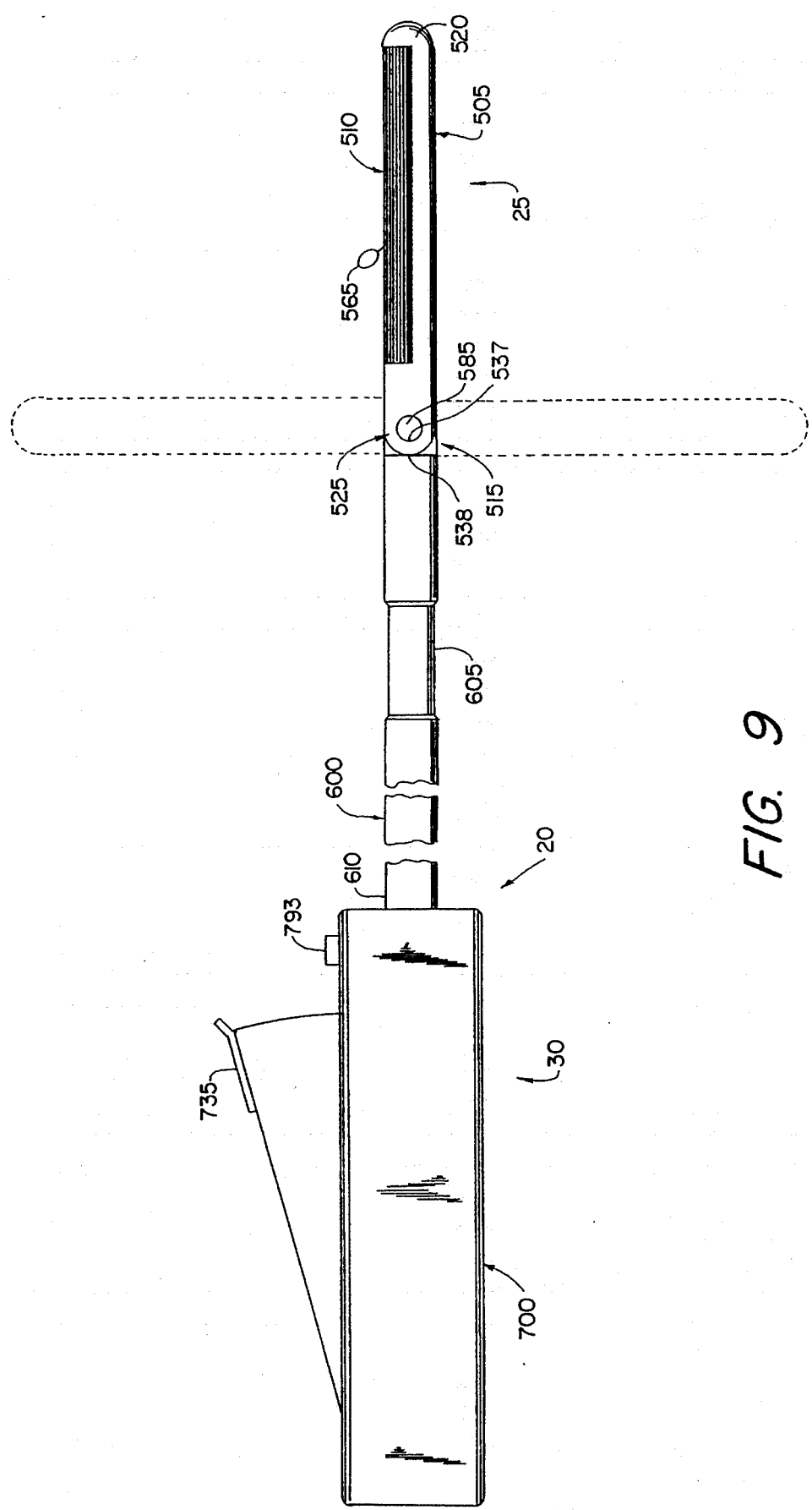
FIG. 9 is a side view of a netting device formed in accordance with the present invention.
Figure 10:
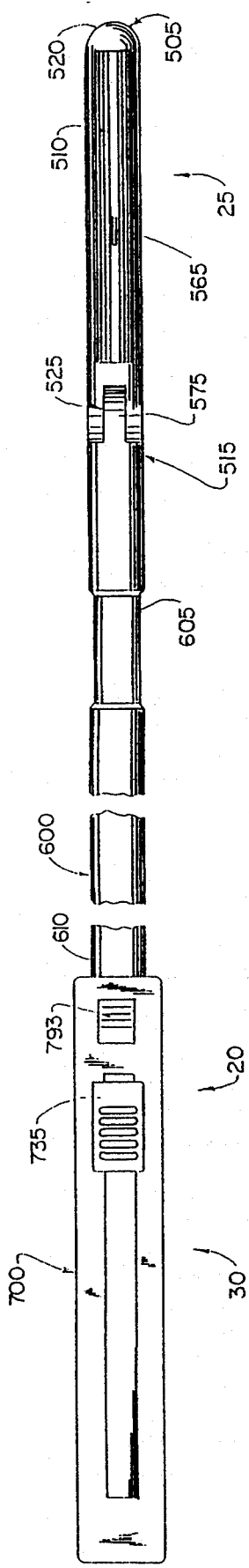
FIG. 10 is a top view of the netting device.
Figure 11:
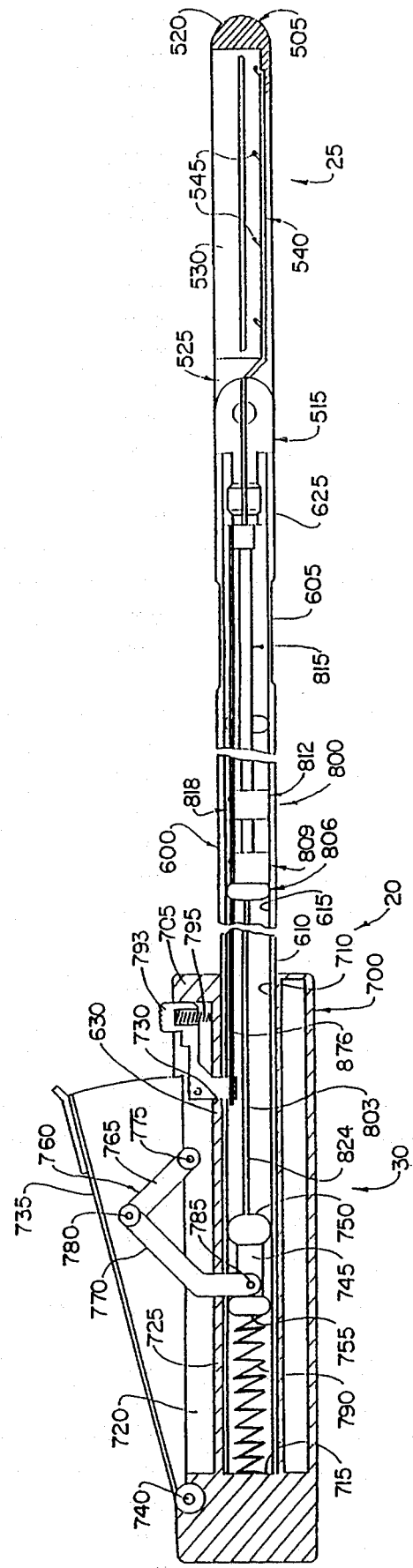
FIG. 11 is a side view in section of the netting device.
Figure 14:
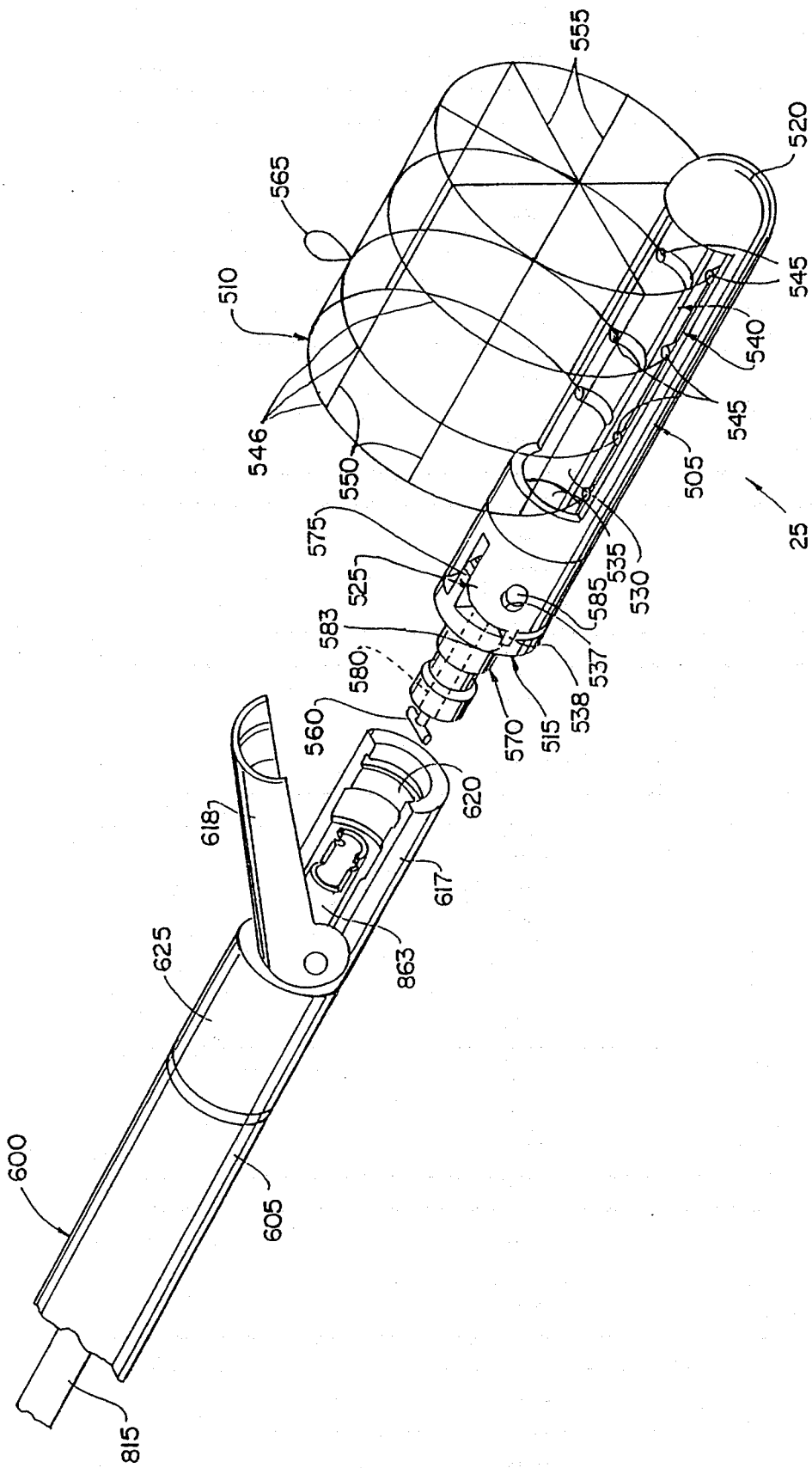
FIG. 14 is a view showing the distal end of the netting device, with the device's net assembly being shown in telescoping relation to the distal end of the device's shaft.
Figure 15:
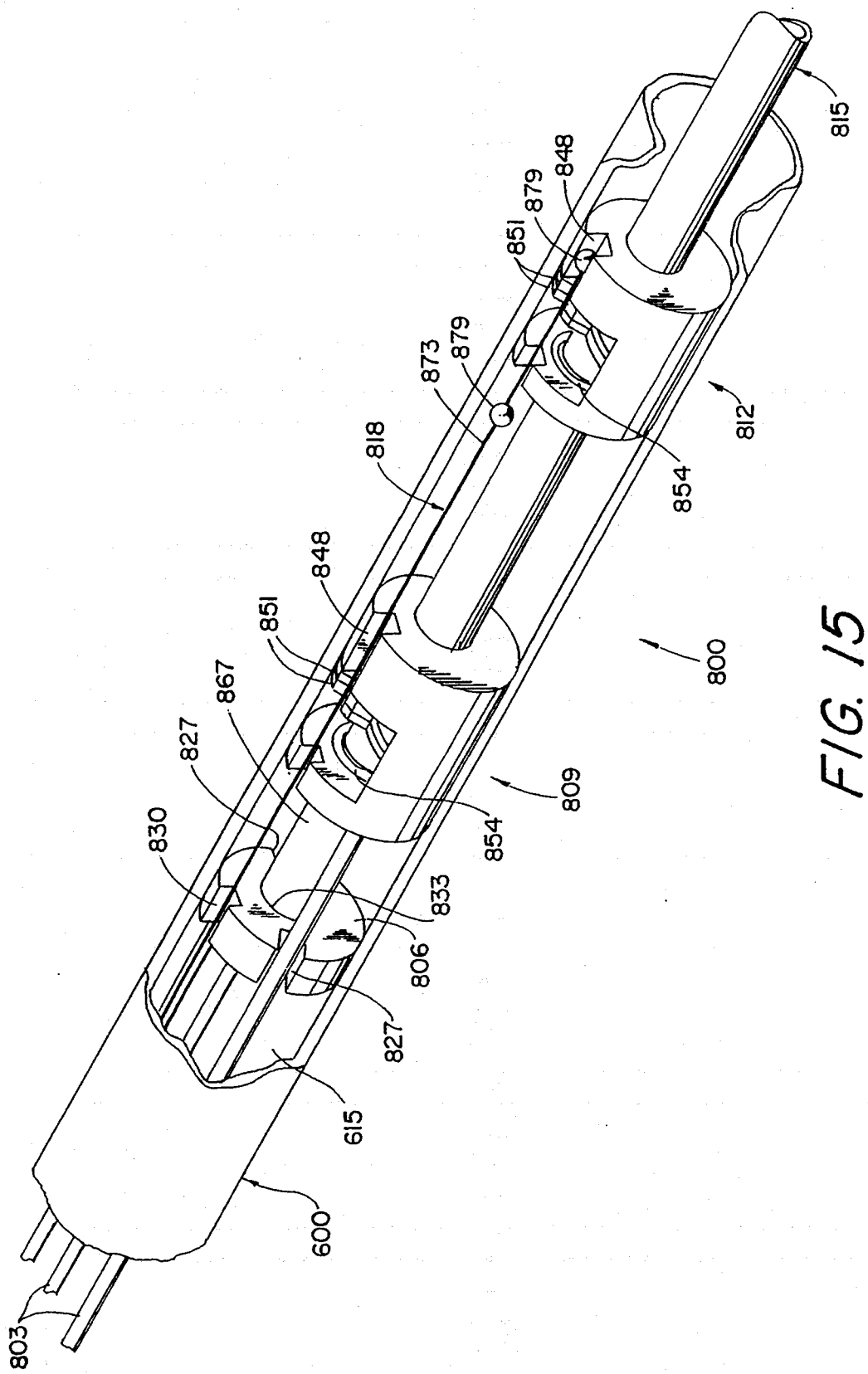
FIG. 15 is an enlarged view showing selected portions of the netting device's retracting assembly.
Figure 16:
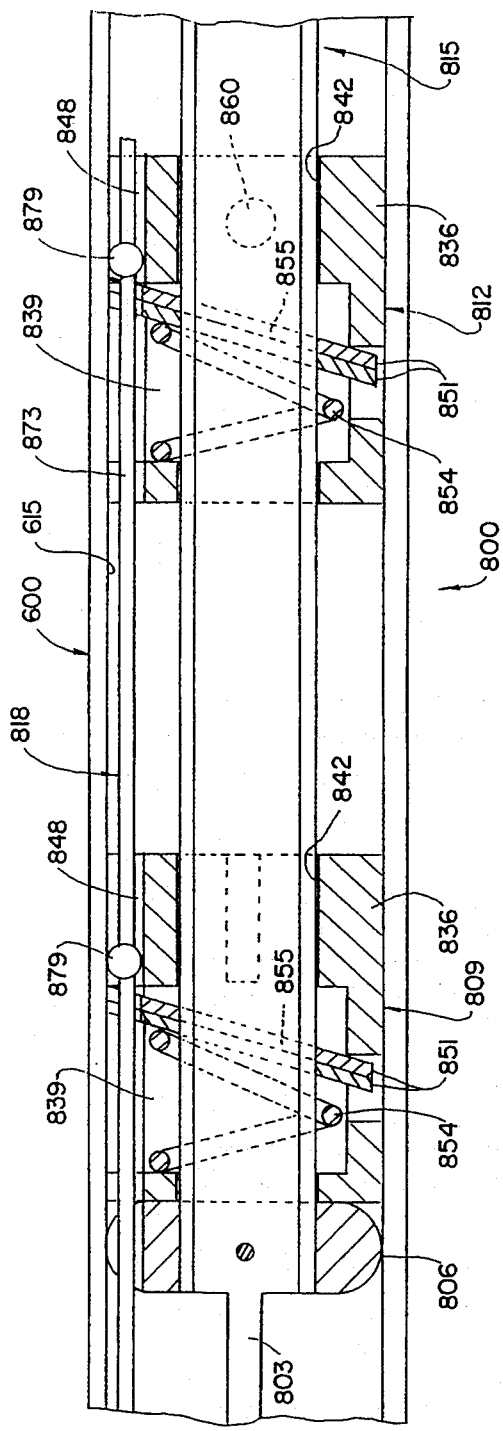
FIG. 16 is a side view in section of selected portions of the netting device's retracting assembly.
Figure 17:
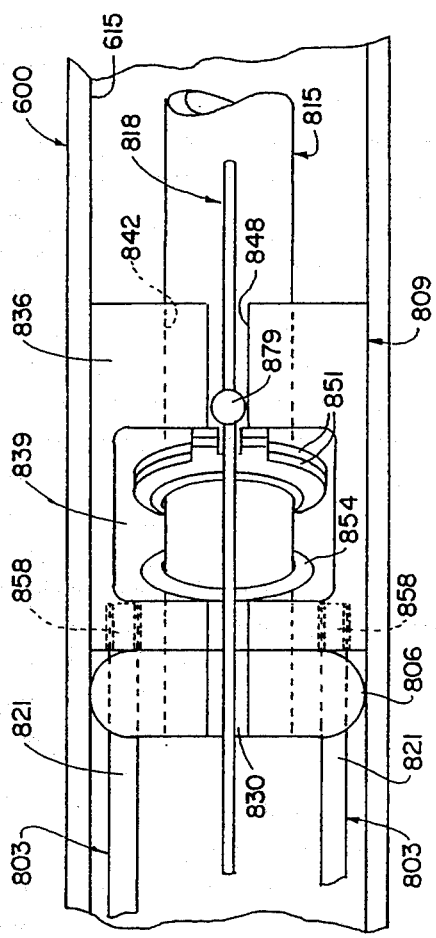
FIG. 17 is a top view of selected portions of the netting device's retracting assembly.
Figure 20:
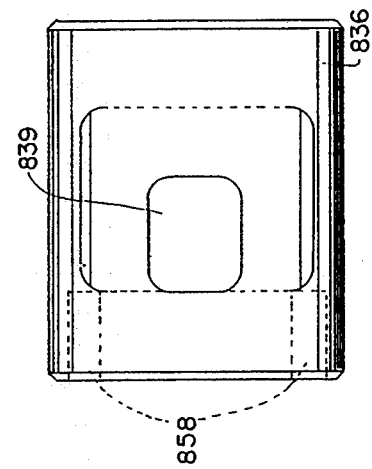
FIG. 20 is a bottom view of the same element shown in FIGS. 18 and 19.
Figure 18:
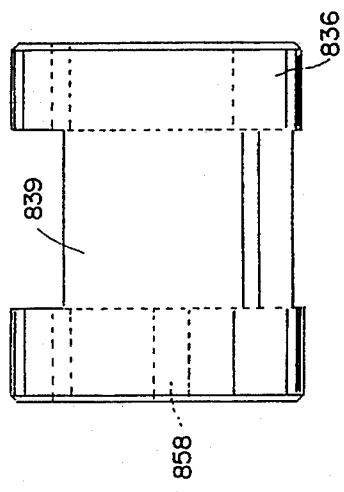
FIG. 18 is a side view of one of the elements utilized in the netting device's retracting assembly.
Figure 19:
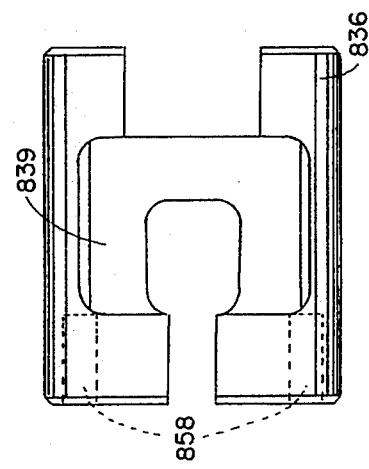
FIG. 19 is a top view of the same element shown in FIG. 18.
Figure 21:
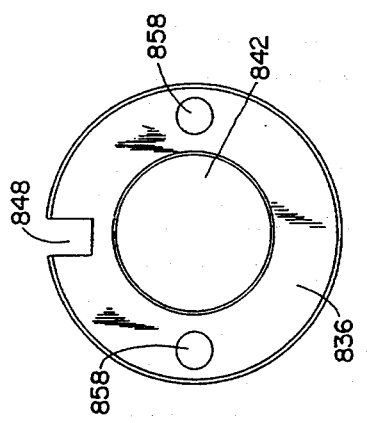
FIG. 21 is an end view of the proximal end of the same element shown in FIGS. 18-20.
Figure 22:
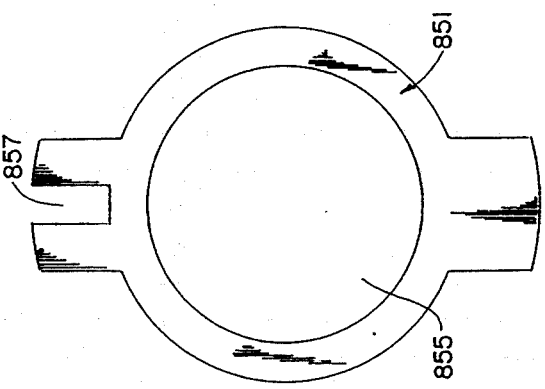
FIG. 22 is an end view of one of the grippers employed in the netting device's retracting assembly.
Figure 23:
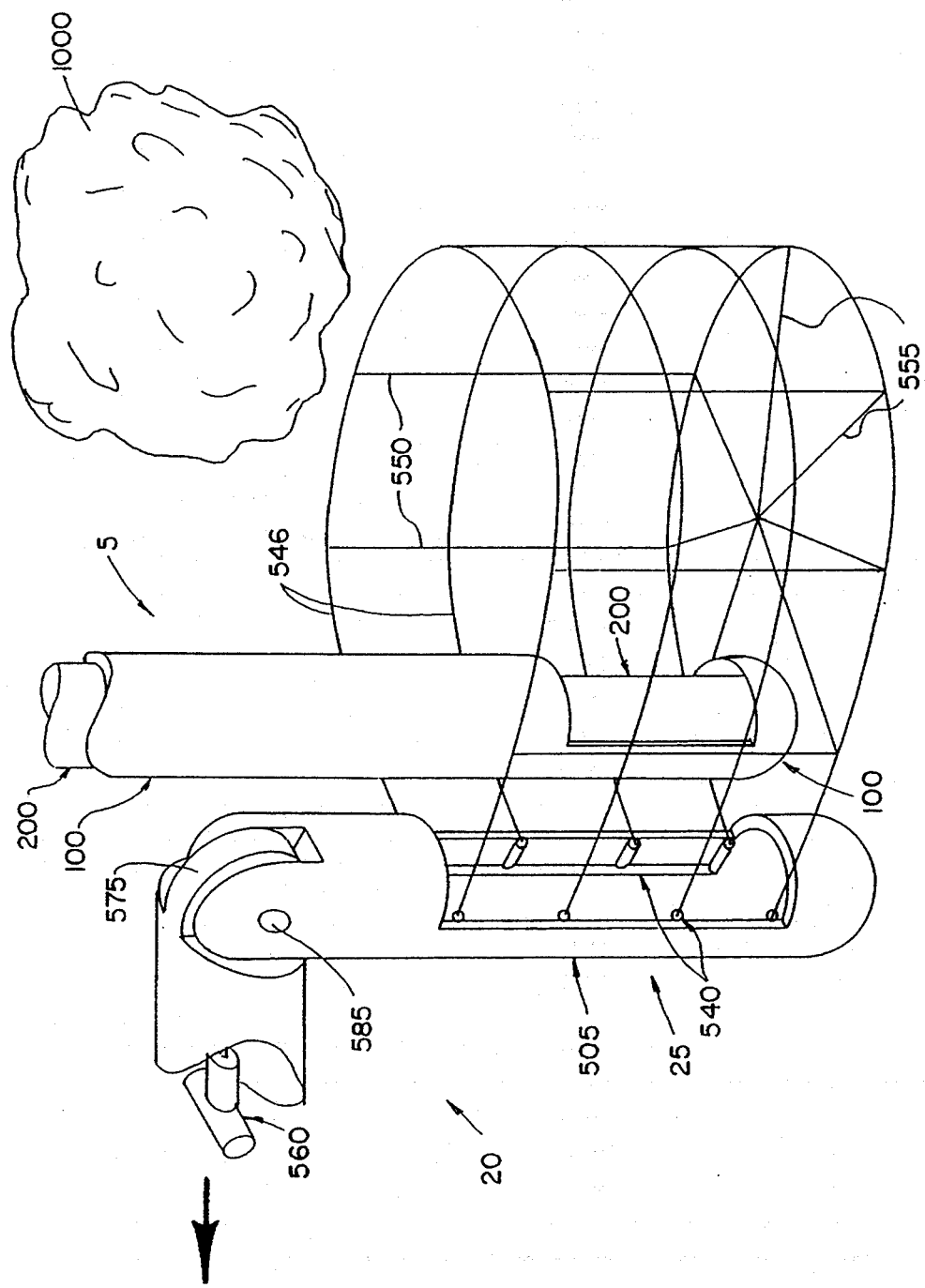
Figure 24:
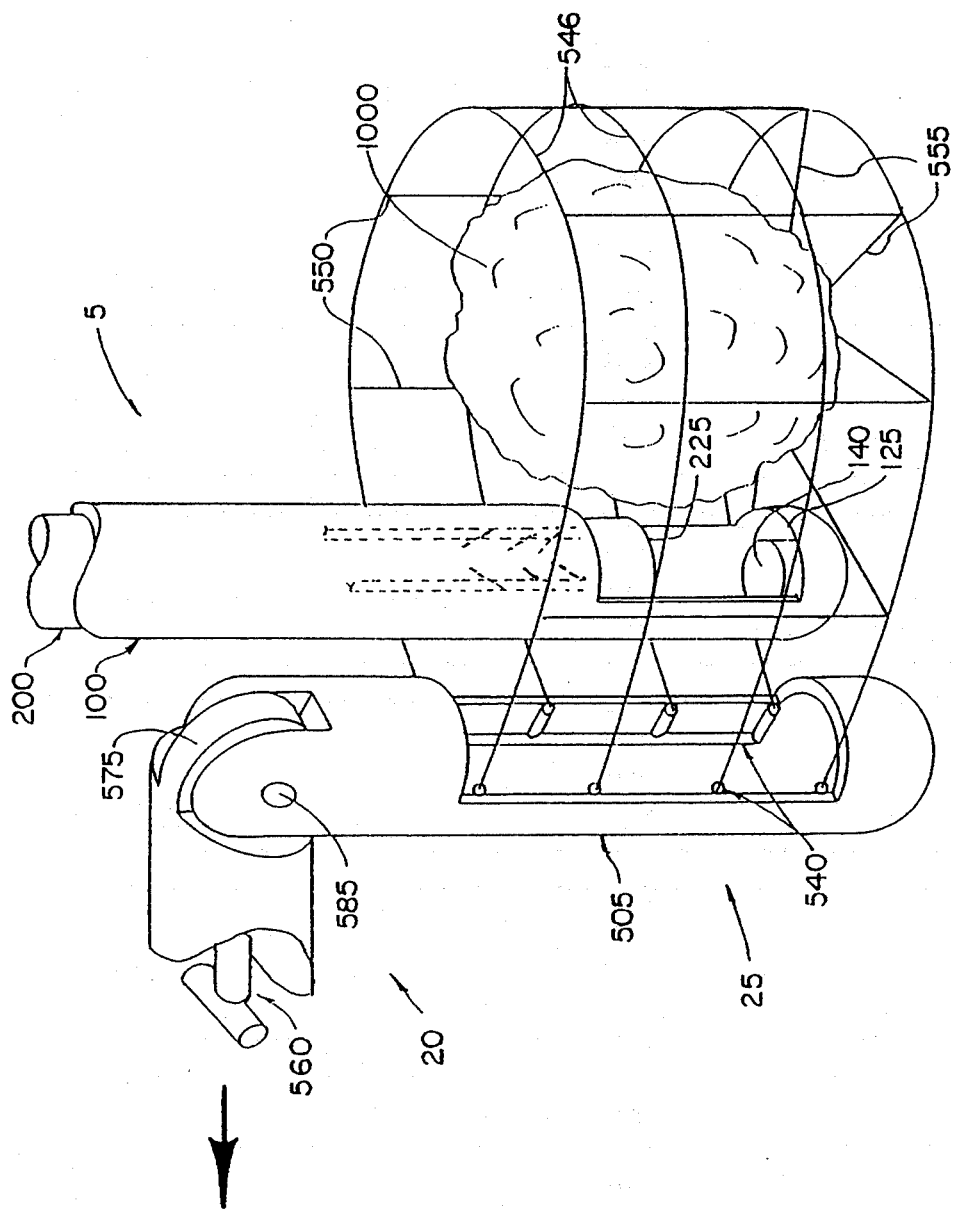
Figure 25:
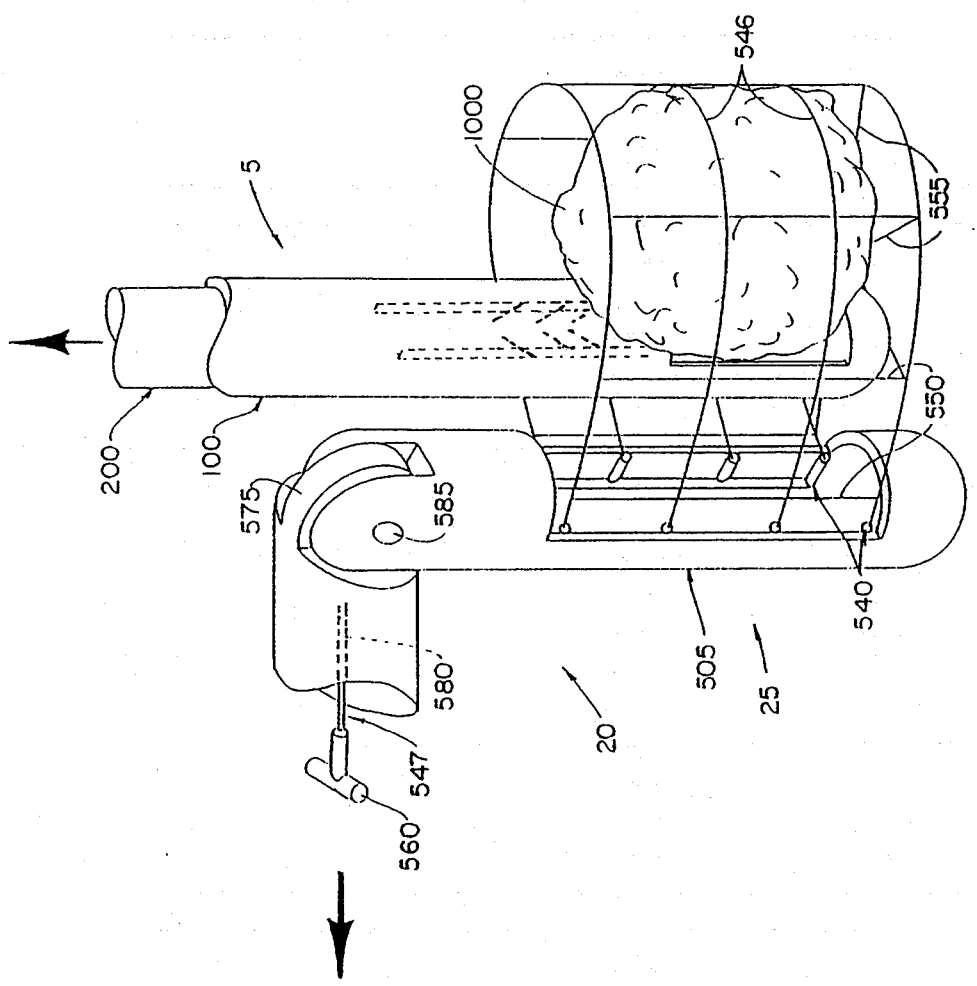
Figure 26:
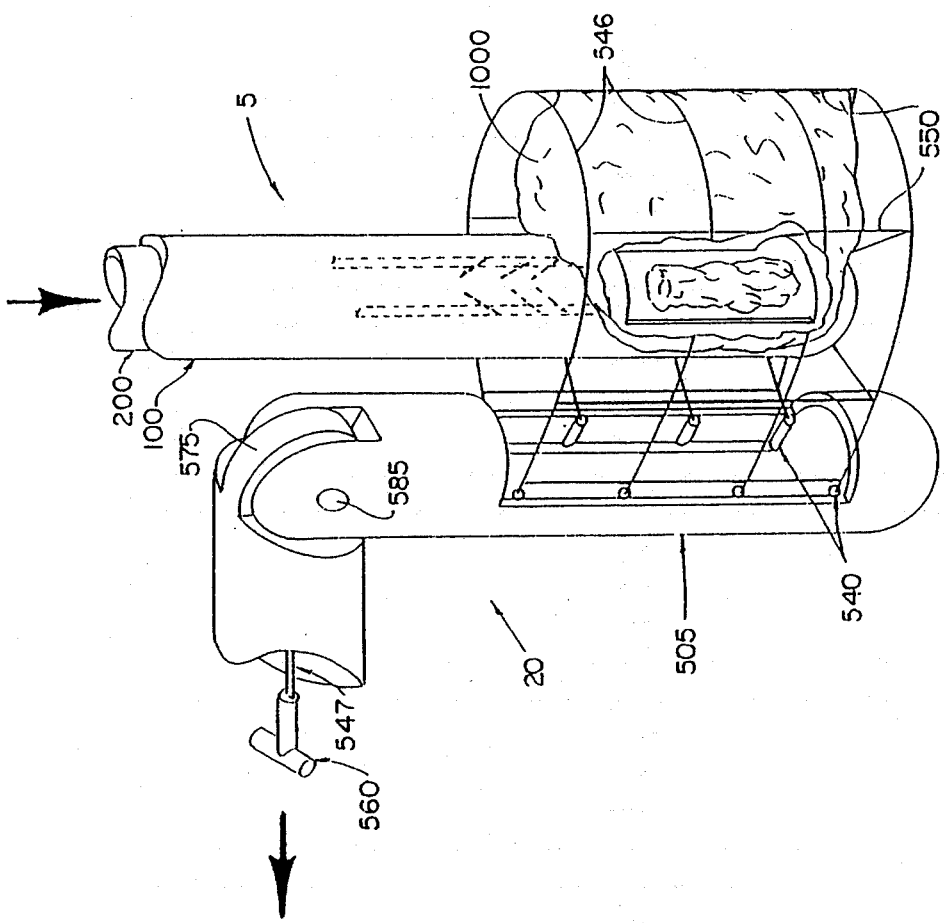
Figure 27:
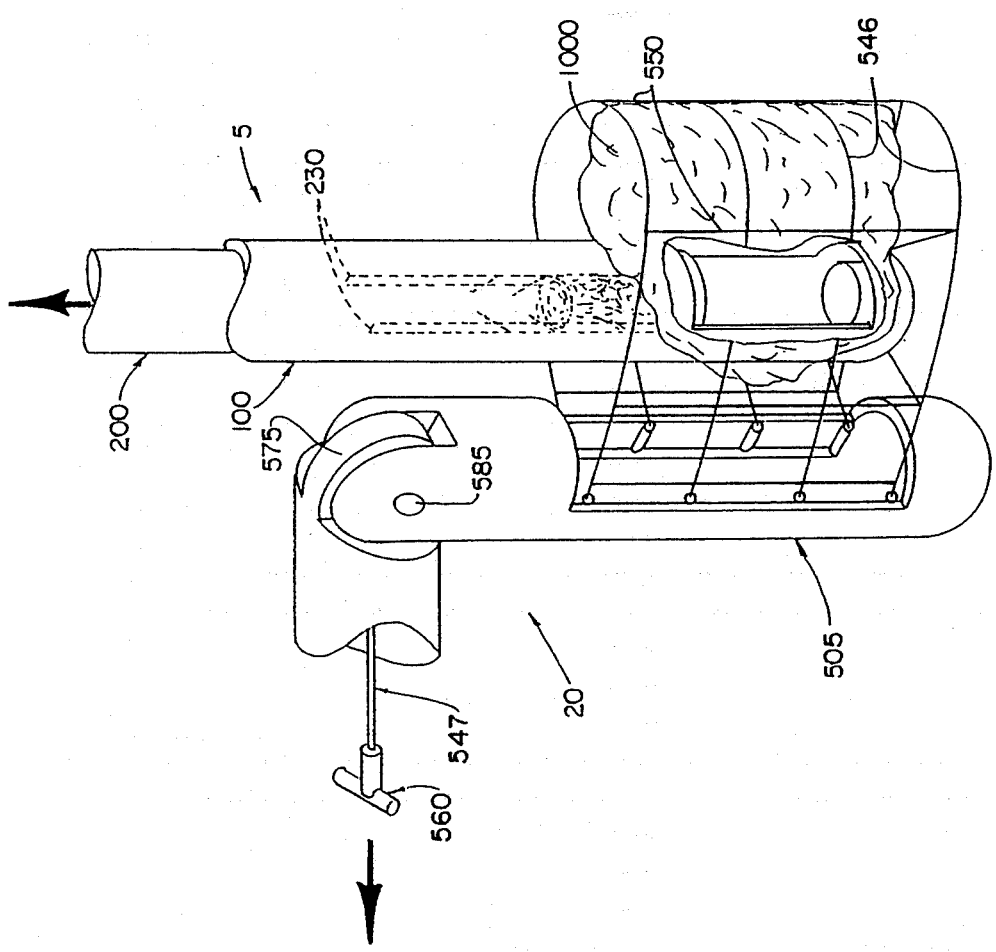

The present invention comprises a morcellator system for use in removing relatively large pieces of tissue from the body during laparoscopic surgery. The morcellator system generally comprises a morcellator device 5 comprising a cutting assembly 10 and a handle assembly 15 (see FIGS. 1-8 and 23-28) and a netting device 20 comprising a netting assembly 25 and a handle assembly 30 (see FIGS. 9-28).

More particularly, and looking now at FIGS. 1-8, morcellator 5 generally comprises the cutting assembly 10 which in turn comprises an outer tube 100 and an inner tube 200, and the handle assembly 15 which in turn comprises fixed handle means 300 and movable handle means 400.

Turning first to cutting assembly 10, outer tube 100 generally comprises a distal end 105, a proximal end 110, and an interior passageway 115. A rectangular distal opening 120 is formed in the distal end of outer tube 100. A sharp cutting edge 125 is provided at the distal end of opening 120. An annular groove 130 is formed in the distal end of outer tube 100. Annular groove 130 starts approximately flush with sharp cutting edge 125 and extends distally thereof. Annular groove 130 defines a cylindrical plug 140. A front knob 145 is disposed on the outer tube's distal end surface 146.

A plurality of barb-receiving bores 147 extend through the wall of outer tube 100. Stationary tissue barbs 150 are disposed in bores 147. Barbs 150 are arranged so that they extend inwardly and proximally from the wall of outer tube 100 so as to project significantly into the interior of outer tube 100. Barbs 150 are formed out of a relatively strong and resilient material, e.g. stainless steel.

Outer tube 100 also comprises an annular proximal end surface 155, and two diametrically-opposed locking pins 160 which extend outwardly from the outer surface of tube 100.

Outer tube 100 is preferably (but not necessarily) formed with a two-part construction, i.e., it is preferably formed out of a metal shaft portion 165 and a plastic shaft portion 170. In the preferred embodiment of the invention, plastic shaft portion 170 is substantially permanently joined to metal shaft portion 165, e.g. during molding. In addition, plastic shaft portion 170 is preferably formed out of a clear plastic material so that the surgeon can visually observe any materials contained within the plastic shaft portion 170.

The morcellator's cutting assembly 10 also comprises an inner tube 200. Inner tube 200 generally comprises a distal end 205, a proximal end 210, and an interior passageway 215. Inner tube 200 terminates in an annular distal surface 220, and in a substantially annular proximal end surface 223. A sharp cutting edge 225 is disposed along at least a portion of distal end surface 220. Two diametrically-opposed, longitudinally-extending slots 230 are formed in the side wall of inner tube 200. Slots 230 are spaced from, and do not intersect, distal surface 220.

Inner tube 200 also comprises a plurality of movable tissue barbs 250. Barbs 250 are arranged so that they extend inwardly and proximally from the wall of inner tube 200 so as to project significantly into the interior of inner tube 200. Barbs 250 are formed out of a relatively strong and resilient material, e.g. stainless steel.

A pair of diametrically-opposed, L-shaped slots 260 are formed at the proximal end of inner tube 200. Each of the L-shaped slots 260 comprises a longitudinally-extending portion 262 and a circumferentially-extending portion 263. The longitudinally-extending portions 262 open on the tube's substantially annular proximal end surface 223.

Inner tube 200 is preferably (but not necessarily) formed with a two-part construction, i.e., it is preferably formed out of a metal shaft portion 265 and a plastic shaft portion 270. In the preferred embodiment of the invention, metal shaft portion 265 is joined to plastic shaft portion 270 by a screw arrangement 275. In addition, plastic shaft portion 270 is preferably formed out of a clear plastic material so that the surgeon can visually observe any materials contained within the plastic shaft portion 270.

Outer tube 100 and inner tube 200 together form cutting assembly 10. To this end, outer tube 100 and inner tube 200 are sized so that inner tube 200 may be telescopically inserted into outer tube 100, with the proximal end of the inner tube protruding out of the proximal end of the outer tube (with the L-shaped slots 260 completely exposed) when the inner tube's distal end surface 220 bottoms out in the outer tube's annular groove 130. In addition, the outer tube's stationary barbs 150 will ride in the inner tube's side wall slots 230 as the inner tube reciprocates between (i) a first position in which the inner tube's distal end surface 220 bottoms out in the outer tube's annular groove 130, and (ii) a second position in which the inner tube's distal end surface 220 is disposed on the proximal side of the outer tube's rectangular distal opening 130 (i.e., in the position shown in FIG. 3). It will be appreciated that the outer tube's barbs 150 are fixed in bores 147 after inner tube 200 has been inserted into outer tube 100.

Turning next to handle assembly 15, fixed handle means 300 generally comprises a body 305 having a central bore 310 and a front counterbore 315. An opening 316 intersects front counterbore 315 so as to define a housing wall 317 which extends about the perimeter of counterbore 315. Central bore 310 and front counterbore 315 together define an annular shoulder 318 at their intersection. A pair of diametrically-opposed side slots 320 extend proximally into body 305 and communicate with front counterbore 315.

Body 305 also comprises a laterally extending wall 330, top and bottom slots 333, and a top opening 335. Top opening 335 is aligned with opening 316, as will hereinafter be described in further detail.

Fixed handle means 300 also comprise a gate assembly 340. Gate assembly 340 in turn comprises a planar body 345. A top button 350 extends out of the top end of planar body 345, and a bottom post 355 extends out of the bottom end of planar body 345. A spring 360 is positioned about, and extends downward from, bottom post 355. An eliptical opening 365 is formed in the central portion of the planar body 345. Two diametrically-opposed side slots 370 communicate with eliptical opening 365. Gate assembly 340 is positioned within housing 305 so that the assembly's planar body 345 extends through housing opening 316, with spring 360 biasing the planar body in an upward direction so that top button 350 protrudes out of housing body 305, and so that the gate assembly's side slots 370 normally are not aligned with housing slots 320. However, it will also be appreciated that the gate assembly's side slots 370 can be selectively aligned with housing slots 320 by appropriately pressing on the gate assembly's top button 350.

Movable handle means 400 generally comprise two handle members 405. Each of the handle members 405 in turn comprises a finger-receiving opening 410, a mounting pin 415 for mounting that handle member to body 305, and a camming slot 420 for connecting that handle member to the remainder of movable handle means 400.

Movable handle means 400 also comprises a linkage assembly 425. Linkage assembly 425 generally comprises a front plug 430 adapted to be partially inserted into the interior of inner tube 200 as will hereinafter be described in further detail, and a pair of diametrically-opposed locking pins 435 which extend outwardly from front plug 430. In addition, linkage assembly 425 also comprises four links 440, 445, 450, and 455. Links 440 and 455 are pinned to one another and to housing 305 by a pin 460. Links 445 and 450 are pinned to one another and to plug 430 by a pin 470. Links 440 and 445 are pinned to each other and to one of the camming slots 420 by a pin 475. Links 450 and 455 are pinned to each other and to the other of the camming slots 420 by a pin 480. A spring 485 is positioned between housing wall 330 and the proximal end of plug 430 so as to bias plug 430 away from housing wall 330. Thus it will be seen that spring 485 normally biases plug 430 distally, however, the user may also overcome that bias and urge the front plug 430 proximally by squeezing handle members 405 together.

Cutting assembly 10 is attached to handle assembly 15 as follows. First, the proximal ends of the assembled tubes 100 and 200 are passed into the housing assembly's front bore 315 so that the diametrically-opposed locking pins 160 on outer tube 100 pass into the two side slots 320 on fixed handle member 305. As the assembled tubes 100 and 200 are passed rearwardly into fixed handle member 305, top button 315 is depressed so as to force the gate assembly's planar body 345 against the power of spring 360 and bring side slots 370 downward into alignment with the handle member's two side slots 320. This will allow the, outer tube's two diametrically-opposed locking pins 160 to slip through gate assembly 340. The assembled tubes 100 and 200 and 200 are then pushed further through eliptical opening 365 until the outer tube's annular proximal end surface 155 engages the handle's annular shoulder 318. This will halt rearward movement of the assembled tubes 100 and 200. As this occurs, the front plug's two diametrically-opposed locking pins 435 enter the two longitudinally-extending portions 262 of L-shaped slots 260 and come to rest adjacent to the circumferentially-extending portions 263. Next, the assembled tubes 100 and 200 are rotated 90 degrees so that (i) the front plug's two diametrically-opposed locking pins 435 are driven into the two circumferentially-extending portions 263 of L-shaped slots 260, thus locking inner tube 200 to front plug 430, and (ii) the outer tube's two diametrically-opposed locking pins 160 are placed into a close sliding engagement with portion 317 of housing 305 and the proximal surface of planar body 345.

As a result of this construction, it will be seen that spring 485 normally biases inner tube 200 forward relative to outer tube 100 so that inner tube 200 bottoms out in annular groove 130 and the outer tube's rectangular distal opening 120 is closed off by inner tube 200. At the same time, squeezing handle members 405 together will cause inner tube 200 to retreat relative to outer tube 100, so that the outer tube's rectangular distal opening 120 will be opened up.

It is to be noted that cutting assembly 10 may be removed from housing assembly 15 after use. This is done by first rotating the assembled tubes 100 and 200 90 degrees so that the longitudinally-extending portions 262 of the inner tube's two L-shaped slots 260 are aligned with the front plug's two locking pins 435, and outer tube's two locking pins 160 are realigned with the handle assembly's side slots 320, then depressing top button 350 so as to realign gate slots 370 with handle slots 320, and then withdrawing the assembled tubes 100 and 200 from body 305.

Morcellator 5 is used as follows. First, the distal end of morcellator 5 is placed next to the relatively large tissue mass which is to be dissected. Then handle members 405 are pulled apart so as to draw inner tube 200 rearwardly, against the power of spring 485, and so as to open up the outer tube's rectangular distal opening 120. Next, morcellator 5 is moved against the tissue mass so that a portion of the tissue mass enters morcellator opening 120. With the assistance of spring 485, handle members 405 are forced together so as to drive inner tube 200 forward, thereby closing the outer tube's window 120. This will cause the sharp edges 125 and 225 to confront one another and thereby sever a piece of tissue off of the relatively large tissue mass. This severed piece of tissue will be contained within the distal end of inner tube 200. Handle members 405 are closed all the way so that the inner tube 200 bottoms out in annular groove 130, and so that the severed piece of tissue engages the outer tube's cylindrical plug 140 and is moved proximally by this engagement until the severed piece of tissue engages the inner tube's tissue barbs 250. Next, handle members 405 are forced apart again, thereby causing inner tube 200 to move proximally once more. This will in turn cause the severed piece of tissue to be impaled on the inner tube's distally-facing barbs 250 and then to be carried proximally with the retreating inner tube. As inner tube 200 moves proximally, the impaled tissue next engages the outer tube's barbs 150. Handle members 405 are forced apart until pins 475 and 480 reach the limit of their travel in camming slots 420. At this point the outer tube's rectangular opening 120 will be opened up again, and the severed piece of tissue will reside on the proximal side of the outer tube's rectangular opening 120. Thereafter, another piece of tissue may be severed from the tissue mass by moving morcellator 5 against the tissue mass so that another portion of the tissue mass enters morcellator opening 120, then forcing handle members 405 together again so as to drive inner tube 200 proximally once more so as to cut off another piece of tissue, etc. In this respect it should be appreciated that as inner tube 200 moves proximally to shear off another piece of tissue, the previously sheared piece of tissue will be impaled on the outer tube's distally facing barbs 150 and thus held against any movement distally with the advancing inner tube 200. As the inner tube moves further distally, the severed piece of tissue will slip off the inner tube's barbs 250 and remain impaled on the outer tube's barbs 150. In this way it will be seen that barbs 150 and 250 together allow severed pieces of tissue to progress proximally down cutting assembly 10 towards handle assembly 15, but prevent the severed tissue from moving distally again with the reciprocating inner tube 200.

Looking next at FIGS. 9–28, netting device 20 generally comprises a netting assembly 25 and a handle assembly 30.

Netting assembly 25 generally comprises a cylindrical body 505, a net 510 and a cylindrical coupling 515.

Cylindrical body 505 generally comprises a rounded distal tip 520, a bifurcated proximal end 525, and a recessed portion 530. An interior passageway 535 extends between the bifurcated proximal end 525 and recessed portion 530, whereby the interior of the recessed portion 530 can communicate with the region proximal to bifurcated proximal end 525. An oval-shaped opening 537 extends across bifurcated proximal end 525, and a tongue 538 extends proximally from bifurcated proximal end 525. A pair of suture manifolds 540 extend from the body's bifurcated proximal end 525 to a plurality of openings 545 which are disposed along the sides of recessed portion 530. Suture manifolds 540 essentially connect openings 545 with interior passageway 535.

Net 510 generally comprises a plurality of circumferentially-extending segments 546 which terminate in proximal end lengths 547, a plurality of longitudinally-extending segments 550, and a plurality of radially-extending segments 555. Circumferentially-extending segments 546 cooperate with longitudinally-extending segments 550 so as to form the side of the net, and radially-extending segments 555 form the bottom of the net. The top of net 510 is open. Proximal end lengths 547 pass through suture manifolds 540, interior passageway 535 and terminate in a T-bar 560 which is disposed proximally of cylindrical coupling 515. A net deployment ring 565 is attached to one of the circumferentially-extending segments 546. In this way it will be seen that by pulling T-bar 560 in a proximal direction, net 510 can be drawn into the cylindrical body's recessed portion 530, and by pulling outwardly on the net deployment ring 565, net 510 can be deployed out of the cylindrical body's recessed portion 530.

Cylinder coupling 515 comprises a stepped outer profile 570, a distal tongue 575, an interior passageway 580, and a groove 583. Distal tongue 575 is sized so as to fit between the bifurcated proximal end 525 of cylindrical body 505, with a connecting pin 585 extending through opening 537 and a corresponding opening (not shown) formed in tongue 575 so as to pivotally connect cylinder coupling 515 to cylindrical body 505. By forming opening 537 with an oval shape and by providing tongue 538 and groove 583, cylindrical body 505 can be locked in alignment with cylinder coupling 515 by aligning tongue 538 and groove 583 and pressing cylindrical body 505 proximally against cylinder coupling 515. At the same time, cylindrical body 505 can be pivoted about relative to cylinder coupling 515 by pulling cylindrical body 505 distally away from cylinder coupling 515 so that tongue 538 is withdrawn from groove 583.

Handle assembly 30 generally comprises a shaft 600, a handle body 700 and a retracting assembly 800.

Shaft 600 generally comprises a distal end 605, a proximal end 610, and an interior opening 615. The distal end of shaft 605 is configured so as to have a fixed lower portion 617 and a hinged upper portion 618. A plurality of counterbores 620 are formed in the distal end of the shaft when fixed lower portion 617 and hinged upper portion 618 are united. A sliding sleeve 625 is disposed about the distal end of shaft 600. Sleeve 625 is adapted to cover or uncover the shaft's hinged upper portion 618, whereby hinged upper portion 618 may be held fast against fixed lower portion 617 or released so as to be able to pivot away from fixed lower portion 617. Counterbores 620 are arranged so as to have a profile corresponding to the stepped outer profile 570 of cylinder coupling 515, whereby sleeve 625 can be slid back, hinged upper portion 618 pivoted away from fixed lower portion 617, cylinder coupling 515 placed against fixed lower portion 617 so that counterbores 620 and stepped outer profile 570 mate, upper portion 618 swung back into engagement with fixed lower portion 617, and sleeve 625 slid forward so as to lock cylinder coupling 515 securely to shaft 600, while still allowing full rotational movement of cylinder coupling 515 relative to the shaft.

Shaft 600 also comprises a proximal opening 630.

The proximal end of shaft 600 is fixed to handle body 700. More particularly, handle body 700 generally comprises a housing 705 and a central bore 710 terminating an end wall 715. A top recess 720 is formed in the top side of housing 705. First and second vertical openings 725 and 730 connect top recess 720 with central bore 710 and the interior of shaft 605, respectively. A trigger 735 is pinned to housing 705 by means of a pin 740. A piston 745, having a distal end surface 750 and a proximal end surface 755, is disposed in central bore 710.

A linkage assembly 760 connects trigger 735 to piston 745. More particularly, linkage assembly 760 comprises a first link 765 and a second link 770. A pin 775 connects link 765 to trigger 735. A pin 780 connects link 765 to link 770. A pin 785 connects link 770 to piston 745. A spring 790 is disposed between end wall 715 and the piston's proximal end surface 755. As a result of this construction, spring 790 normally biases piston 745 distally and trigger 735 upwards, away from housing 705; however, by pressing trigger 735 downward, linkage assembly 760 will force piston 745 to move proximally against the force of spring 790.

Handle assembly 700 also comprises a release button 793 and a spring 795. Spring 795 normally biases release button 793 upwards, as will hereinafter be discussed in further detail.

Retracting assembly 800 generally comprises a pair of piston rods 803, a guide ring 806, an advancing mechanism 809, a holding mechanism 812, a connecting rod 815, and a release rod 818.

Piston rods 803 each comprise a distal end 821 and a proximal end 824. Piston rods 803 are connected at their distal ends to advancing mechanism 809, and at their proximal ends to piston 745. In this way it will be seen that as piston 745 reciprocates back and forth within bore 710 under the influence of trigger 735 and spring 790, advancing mechanism 809 will also be moved back and forth within shaft 600.

Guide ring 806 is a disk-like device fixed in place within shaft 600. Guide ring 806 comprises a pair of side notches 827, a top notch 830, and a central opening 833. Side notches 827 accommodate and help stablize rods 803 as they move back and forth within shaft 600. Top notch 830 accommodates and helps stablize release rod 818 as it also moves back and forth within shaft 600, as will hereinafter be described in further detail. The guide ring's central opening 833 accommodates and helps stabilize connecting rod 815 as the connecting rod is advanced toward the proximal end of netting device 20, as will hereinafter be described in further detail.

Advancing mechanism 809 and holding mechanism 812 are substantially identical to one another, except that advancing mechanism 809 is attached to piston rods 803 and moves within shaft 600, whereas holding mechanism 812 is fixedly attached to the interior of shaft 600. Advancing mechanism 809 and holding mechanism 812 each generally comprise a body 836 having a central cavity 839, a central opening 842, and a top groove 848. A plurality of grippers 851 and a spring 854 are disposed in each body 836. Each gripper 851 includes a central opening 855 and a top slot 857. The distal ends of piston rods 803 are screwed into a pair of threaded bores 858 formed in the body 836 of advancing mechanism 809. A locking pin 860 locks the body 836 of locking mechanism 809 to shaft 600.

Springs 854 in advancing mechanism 809 and holding mechanism 812 normally bias their associated grippers 851 into an inclined position so that they bind with connecting rod 815. At the same time, grippers 851 can overcome the bias of springs 854 so as to assume a vertical position, in which case connecting rod 815 can pass cleanly through the central openings 854 of the grippers. On account of this construction, when piston rods 803 are moved proximally within shaft 600 by a retreating piston 745, the advancing mechanism's grippers 851 will engage connecting rod 815 and pull it proximally within the shaft. As this occurs, the holding mechanism's grippers 851 will pivot within their body 836 so as to assume a vertical position and thereby allow the shaft to move proximally relative to holding mechanism 812. In a corresponding manner, when piston rods 803 are moved distally within shaft 600 by an advancing piston 745, the holding mechanism's grippers 851 will bind with connecting rod 815 so as to prevent the connecting rod from moving distally within shaft 600. As this occurs, the advancing mechanism's own grippers 851 will assume a vertical position so as to permit the advancing mechanism's body 836 to move relative to the stablized connecting rod 815. In this way it will be seen that advancing mechanism 809 and holding mechanism 812 can coact to permit connecting rod 815 to be incrementally moved toward handle body 700 as piston 745 reciprocates back and forth within housing 705.

Connecting rod 815 itself comprises a distal end 863 and a proximal end 867. Distal end 863 includes a cut away profile that is adapted to grasp the netting assembly's T-bar 560. In this way it will be seen that as connecting rod 815 is moved proximally within shaft 600 by retracting asssembly 800, T-bar 560 will be drawn proximally as well so as to retract net 510 into cylindrical body 505.

Retracting assembly 800 also comprises a release rod 818. Release rod 818 comprises a distal end 873, a proximal end 876, and release means 879. The proximal end of release rod 818 is connected to release button 793 so that release rod 818 will be moved proximally when release button 793 is depressed. Release rod 818 passes through the guide ring's top notch 830 and the top slots 857 in grippers 851 of advancing mechanism 809 and holding mechanism 812. Release means 879 preferably takes the form of several enlargements placed along the length of release rod 818. Release means 879 are disposed on release rod 818 so that they will normally lie on the distal side of grippers 851 in advancing mechanism 809 and holding mechanism 812. However, by depressing button 793, release rod 818 may be forced in a proximal direction whereby release means 879 will engage and force grippers 851 into a vertical orientation. In this way it will be seen that by depressing release button 793, the advancing mechanism 809 and the holding mechanism 812 may be forced to release the hold they will normally exert on connecting rod 815.

As a result of the foregoing construction, it will be seen that by depressing release button 793 and pulling net deployment ring 565, net 510 may be deployed out of the cylindrical body's recessed portion 530. At the same time, however, pulling on trigger 735 will cause the retracting assembly 800 to progressively draw T-bar 560 in a proximal direction, whereby net 510 will be retracted back into cylindrical body 505.

Netting device 20 is used as follows. First its distal end is placed close to the tissue mass which is to be netted by the device. Next, release button 793 is depressed and another tool (e.g. such as the front knob 145 of the morcellator 5 previously disclosed) is used to deploy net 510 from netting device 20. Then netting device 20 is manipulated so as to slip net 510 over the tissue mass and thereby engulf the same. Thereafter, trigger 735 is pressed a number of times so as to retract the net 510 back into cylindrical body 505 and thereby securely capture the tissue mass. FIGS. 23-28 show morcellator 5 and netting drive 20 dissecting a mass of tissue 1000 in accordance with the present invention.

What is claimed is:

1. A morcellator comprising:
   an outer tube having a distal end terminating in a distal end surface, a proximal end, an internal passageway extending from said distal end to said proximal end, and an opening formed in said distal end and communicating with said internal passageway;
   an inner tube having a distal end terminating in a distal end surface adapted for morcellating tissue, a proximal end, and an interior passageway connecting said distal end of said inner tube with said proximal end of said inner tube, said inner tube being sized to make a close sliding fit within said outer tube;
   a handle assembly comprising a body and actuating means, said proximal end of said outer tube being attached to said body, and said proximal end of said inner tube being attached to said actuating means, with said actuating means being adapted to move said inner tube between (1) a first position wherein said opening formed in said distal end of said outer tube is closed off by said inner tube, and (2) a second position wherein said opening formed in said distal end of said outer tube is at least part way open;
   first tissue holding means projecting into said interior passageway of said inner tube for permitting tissue to move proximally through said inner tube, and preventing tissue from moving distally through said inner tube; and
   second tissue holding means projecting into said interior passageway of said inner tube for permitting tissue to move proximally through said outer tube, and preventing tissue from moving distally through said outer tube.

2. A morcellator according to claim 1 wherein said opening in said outer tube distal end comprises a sharp cutting edge.

3. A morcellator according to claim 2 wherein said distal end of said outer tube comprises a cylindrical plug extending within said internal passageway proximally from said distal end of said outer tube, and an annular groove between said plug and said outer tube, said groove and said plug being substantially flush with said sharp cutting edge, said cylindrical plug being adapted for pushing said tissue into engagement with said first tissue holding means.

4. A morcellator according to claim 1 wherein a knob is disposed on said outer tube's distal end.

5. A morcellator according to claim 1 wherein said second tissue holding means comprise a plurality of inwardly and proximally extending barbs arranged so as to project into said interior passageway of said inner tube.

6. A morcellator according to claim 5 wherein two diametrically-opposed, longitudinally-extending slots are formed in said inner tube distal end and further wherein said slots are spaced from, and do not intersect said inner tube distal end surface so as to provide access for said plurality of barbs into said interior passageway of said inner tube.

7. A morcellator according to claim 6 wherein said distal end of said outer tube comprises a plurality of barb-receiving bores.

8. A morcellator according to claim 6 wherein said plurality of barbs are stationary with respect to said outer tube.

9. A morcellator according to claim 6 wherein said barbs are formed out of a relatively strong and resilient material.

10. A morcellator according to claim 1 wherein said outer tube comprises a metal portion and a plastic portion.

11. A morcellator according to claim 10 wherein said plastic portion is permanently joined to said metal portion.

12. A morcellator according to claim 10 wherein said plastic portion is transparent.

13. A morcellator according to claim 1 wherein said inner tube comprises a sharp cutting edge disposed along at least a portion of said inner tube distal end surface.

14. A morcellator according to claim 1 wherein said first tissue holding means comprise at least one barb disposed adjacent to said inner tube distal end surface.

15. A morcellator according to claim 14 wherein said at least one barb is arranged so as to extend inwardly and proximally of said inner tube interior passageway.

16. A morcellator according to claim 15 wherein said at least one barb is movable with respect to said outer tube.

17. A morcellator according to claim 15 wherein said at least one barb is formed out of a relatively strong and resilient material.

18. A morcellator according to claim 1 wherein said inner tube comprises a metal portion and a plastic portion.

19. A morcellator according to claim 18 wherein said metal portion and said plastic portion are releasably fastened together.

20. A morcellator according to claim 18 wherein said plastic portion comprises a transparent material.

* * * * *